US00PP27157P2

(12) United States Plant Patent
Bergs

(10) Patent No.: US PP27,157 P2
(45) Date of Patent: Sep. 13, 2016

(54) ***LAVANDULA* PLANT NAMED 'LOWI2010-05'**

(50) Latin Name: ***Lavandula stoechas* ssp. *lusitanica***
Varietal Denomination: LOWI2010-05

(71) Applicant: Wim Bergs, Heythuysen (NL)

(72) Inventor: Wim Bergs, Heythuysen (NL)

( * ) Notice: Subject to any disclaimer, the term of this patent is extended or adjusted under 35 U.S.C. 154(b) by 37 days.

(21) Appl. No.: 14/544,885

(22) Filed: Mar. 2, 2015

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — Penny J. Aguirre

(57) ABSTRACT

A new cultivar of *Lavandula stoechas*, 'LOWI2010-05', that is characterized by its upright and compact plant habit with strong stems, its inflorescences with fertile flowers that are deep violet-blue in color and large sterile bracts that are violet-purple in color, its late commencing and long blooming habit, its good retention of color after transportation without light, and its strong resistance against downy mildew.

2 Drawing Sheets

Botanical classification: *Lavandula stoechas* ssp. *lusitanica*.

Variety denomination: 'LOWI2010-05'.

BACKGROUND OF THE INVENTION

The present invention relates to a new and distinct cultivar of *Lavandula stoechas* ssp. *lusitanica* and will be referred to hereafter by its cultivar name, 'LOWI2010-05'. 'LOWI2010-05' is a new variety of lavender suitable for landscape and container use.

The inventor discovered the new cultivar, 'LOWI2010-05', as a chance seedling in a seed plot in Boskoop, the Netherlands in August of 2010. The seedbed had been planted with seeds collected from an open-pollinated, unpatented, and unnamed plant of *Lavandula stoechas* ssp. *lusitanica*. The male parent is unknown.

Asexual reproduction of the new cultivar was first accomplished by the Inventor by stem cuttings in Heythuysen, the Netherlands in September of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new lavender. These attributes in combination distinguish 'LOWI2010-05' as a unique cultivar of lavender.

1. 'LOWI2010-05' exhibits an upright and compact plant habit with strong stems.
2. 'LOWI2010-05' exhibits inflorescences with fertile flowers that are deep violet-blue in color and large sterile bracts that are violet-purple in color.
3. 'LOWI2010-05' blooms later and for a longer period than is typical of plants of *Lavandula stoechas*; from late spring to late summer in The Netherlands.
4. 'LOWI2010-05' exhibits inflorescenses with good retention of color after transportation without light (a frequent problem with cultivars of *Lavandula stoechas*).

5. 'LOWI2010-05' exhibits strong resistance against downy mildew.

The female parent plant of 'LOWI2010-05' differs from 'LOWI2010-05' in having a less compact plant habit, in having weak stems, and in having inflorescences with sterile bracts that are smaller in size. 'LOWI2010-05' can be most closely compared to the *Lavandula stoechas* ssp. *lusitanica* cultivars 'Lusi Purple' (not patented) and 'Wijs02' (U.S. Plant Pat. No. 25,001). Both cultivars are similar to 'LOWI2010-05 in having late, long bloom periods and in being suitable for transportation. 'Lusi Purple' differs from 'LOWI2010-05' in having inflorescences with dark purple fertile flowers and light purple sterile bracts. 'Wisj02' differs from 'LOWI2010-05' in having inflorescences with purple-blue fertile flowers and pink sterile bracts and in having a more columnar plant habit.

BRIEF DESCRIPTION OF THE DRAWINGS

The accompanying colored photographs illustrate the overall appearance and distinct characteristics of the new lavendar.

The photographs were taken of a 10-month-old plant of the new cultivar as grown outdoors in a 17-cm container in Boskoop, The Netherlands.

Figure 1:
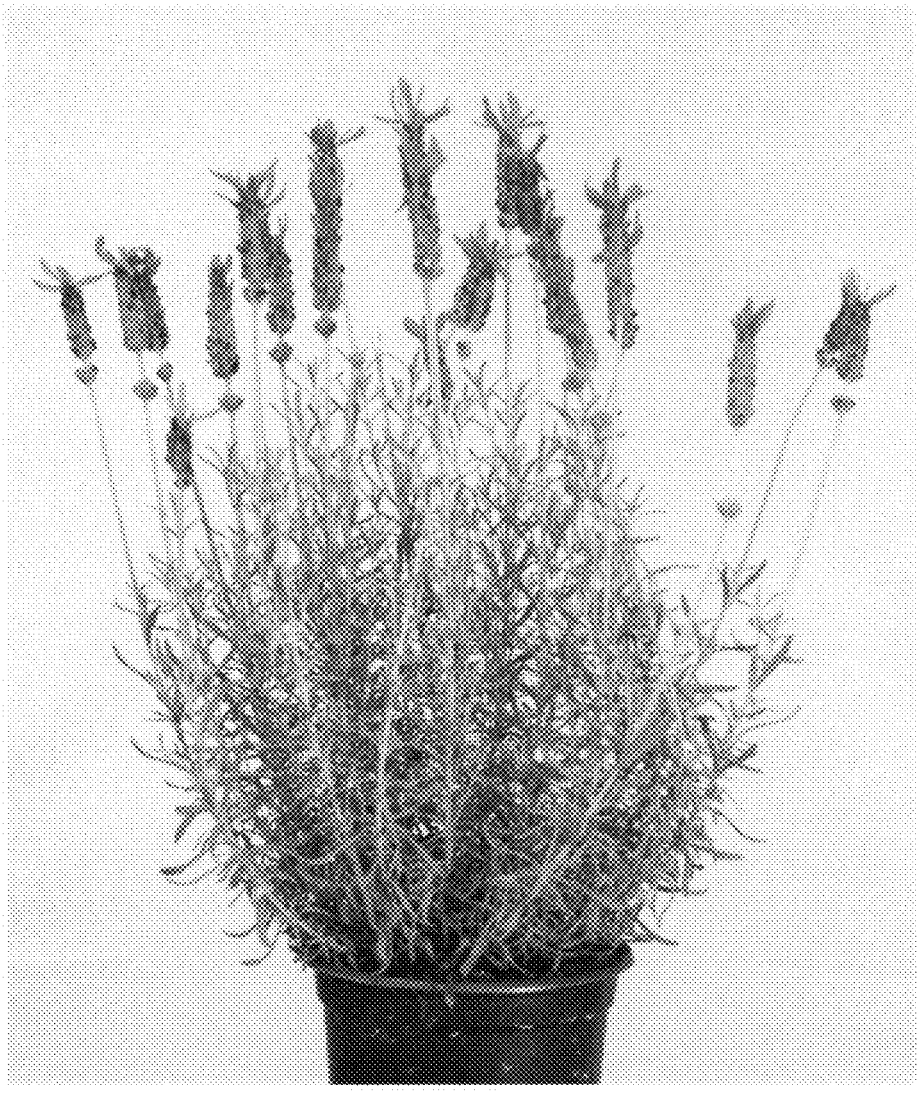

The photograph in FIG. 1 provides a side-view of 'LOWI2010-05' in bloom.

Figure 2:
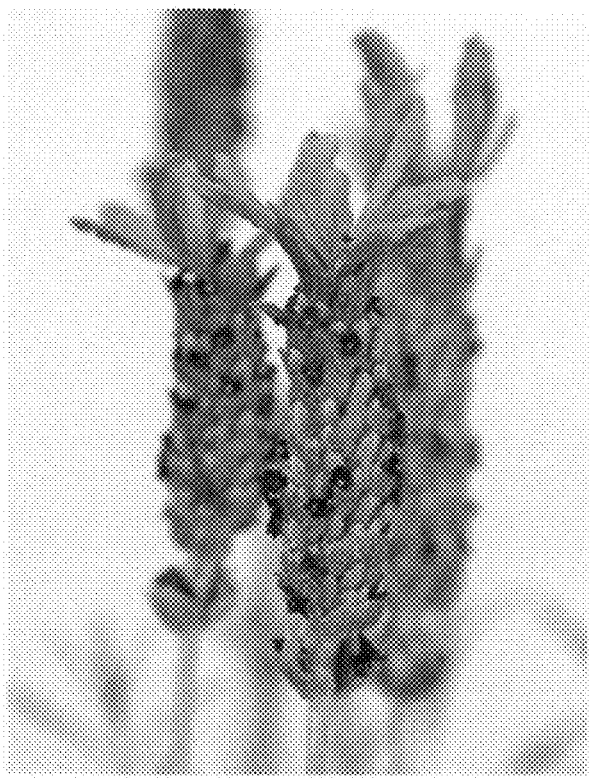

The photograph in FIG. 2 provides a close-up view of an inflorescence of 'LOWI2010-05'.

Figure 3:
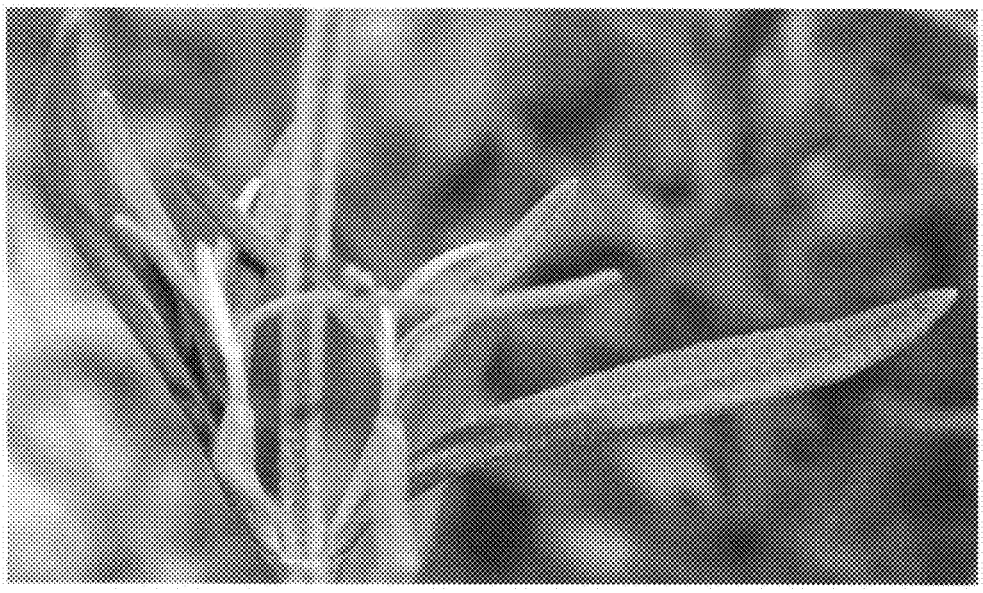

The photograph in FIG. 3 provides a close-up view of the foliage of 'LOW12010-05'.

The colors in the photographs are as close as possible with the digital photography techniques available, the color values cited in the detailed botanical description accurately describe the colors of the new lavender.

DETAILED BOTANICAL DESCRIPTION

The following is a detailed description of 10 month-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Late to commence bloom and long blooming; late spring to late summer in The Netherlands.

*Plant type.*—Perennial herb.

*Plant habit.*—Oblong form with broadly upright lateral branches.

*Height and spread.*—An average of 31 cm in height and 30.3 cm in spread.

*Cold hardiness.*—At least to U.S.D.A. Zone 7.

*Diseases and pests.*—Strong resistance observed against downy mildew (*Peronospora* spp.) has been observed, no particular susceptibility or resistance to pests has been observed.

*Root description.*—Densely fibrous, freely branched.

*Propagation*—Stem cuttings.

*Growth.*—Moderate, grows approximately 10 cm per month in the spring.

Stem description:

*Stem shape.*—Quadangular.

*Stem color.*—144C to 144D.

*Stem surface.*—Dull, glabrous, and densely covered with small glands; <0.1 mm in diameter and 144C to 144D in color.

*Stem size.*—An average of 14.2 cm in length and 1.2 cm in diameter.

*Stem strength.*—Strong.

*Branching.*—Freely branched with an average of 25 lateral branches.

Foliage description:

*Leaf shape.*—Linear.

*Leaf division.*—Simple.

*Leaf base.*—Cuneate.

*Leaf apex.*—Acute.

*Leaf venation.*—Pinnate, color; upper surface 194A and lower surface 147D.

*Leaf margins.*—Entire, moderatley revolute.

*Leaf arrangement.*—Opposite.

*Leaf attachment.*—Sessile.

*Leaf number.*—An average of 34 (17 pairs) per lateral branch.

*Leaf surface.*—Upper and lower surface; dull and densely covered with small glands; <0.1 mm in diameter and 137B to 137C in color.

*Leaf size.*—An average of 4.1 cm in length and 4 mm in width.

*Leaf internode length.*—Average of 1.2 cm in length.

*Leaf color.*—Young upper surface; 138A, young lower surface; 138B, mature upper surface; 137B, mature lower surface; 137C.

*Leaf fragrance.*—Strongly fragrant, typical *Lavandula* scent.

Inflorescence description:

*Inflorescence type.*—Small flowers arranged in compact terminal spikes with showy terminal sterile bracts.

*Inflorescence number.*—1 per lateral stem.

*Inflorescence fragrance.*—No fragrance.

*Lastingness of inflorescence.*—An average of 10 days.

*Inflorescence size.*—An average of 7.1 cm in height and 1.6 cm in width, terminal spikes are an average of 3.5 cm in width.

*Flowers.*—Outward aspect, self-cleaning, salverform in shape, with one upper lip (split into two identical lobes) and one lower lip (split into three lobes, identical to upper lip lobes) since the lobes are identical, they are described as petals, 3.5 mm in diameter and 8 mm in depth, an average of 150 flowers per inflorescence.

*Flower buds.*—An average of 6 mm in length and 12 mm in diameter, narrow-oblong in shape, color; 145B with apex 90A.

*Petals.*—Dull and glabrous on all surfaces, rotate in arrangement, 2 (upper lip split in 2 lobes, lower lip split in 3 lobes; all lobes are identical in shape and color), spathulate in shape, lower 75% of petals are fused into tube, entire margin, rounded apex, an average of 7 mm in length and 0.15 mm in width, color: upper and lower surface of petal when opening and fully opened; 90A with tube NN155D, color fades to N89B.

*Sepals.*—Linear in shape and fused into campanulate tube, entire magin, acute apex, fused base, 5 mm in length and 0.75 mm in width, color; young upper and lower surfaces 145B to 145C, mature upper and lower surfaces 145A, both surfaces; dull and moderately covered with woolly tomentose hairs; 0.5 mm in length and NN155D in color.

*Calyx.*—Campanulate in shape, 4 mm in length and 1.5 mm in diameter.

*Peduncles.*—Strong, quadrangular in shape, an average of 13.2 cm in length and 2 mm in diameter, held at an average angle of 0° (straight on top of lateral branch), color; 137B with edges 138C, surface; dull, glabrous, and densely covered with small glands; <0.1 mm in diameter and 144C to 144D in color.

*Pedicels.*—Not present, individual flowers are sessile.

*Bracts.*—Fertile; 1 per 7 flowers, broad rhomboidal in shape, entire margins, aristate apex, cuneate base, an average of 8 mm in length and width, both surfaces; dull, 144D in color, veins 137D in color, both surfaces moderately covered with woolly tomentose hairs an average of 0.5 mm in length and NN155D in color, sterile; an aveage of 10 at top of each spike, narrow oblanceolate in shape, undulate margins, broad apex, cuneate base, an average of 2.3 cm in length and 7 mm in width, both surfaces; N82A to N82B in color and matt and glabrous.

Reproductive organs:

*Pistils.*—1, an average of 3 mm in length, stigma is club-shaped and N92A in color, style is an average of 0.2 mm in length and N155A in color, ovary is 143B in color.

*Stamens.*—4, anthers; dorsifixed, kidney-shaped, an average of 0.5 mm length and N186A to N186B in color, the filament is implanted in petal and 0.5 mm in length, pollen is low in abundance and 17B in color.

*Fruit and seeds.*—Not observed.

It is claimed:

1. A new and distinct cultivar of *Lavandula* plant named 'LOWI2010-05' as herein illustrated and described.

* * * * *